US00PP34179P2

(12) United States Plant Patent
Mowrey et al.

(10) Patent No.: US PP34,179 P2
(45) Date of Patent: May 3, 2022

(54) BLUEBERRY PLANT NAMED 'DRISBLUETWENTYSIX'

(50) Latin Name: ***Vaccinium corymbosum* L.**
Varietal Denomination: DrisBlueTwentySix

(71) Applicant: Driscoll's, Inc., Watsonville, CA (US)

(72) Inventors: Bruce D. Mowrey, Watsonville, CA (US); Esther J. Kibbe, Watsonville, CA (US); Marta C. Baptista, Watsonville, CA (US); Raymond L. Jacobs, III, Watsonville, CA (US); Maria Velarde, Watsonville, CA (US); James Olmstead, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 17/204,426

(22) Filed: Mar. 17, 2021

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 5/02; A01H 5/08
See application file for complete search history.

(56) References Cited

U.S. PATENT DOCUMENTS

| | | | |
|---|---|---|---|
| PP6,699 | P | 3/1989 | Wood |
| PP11,807 | P2 | 3/2001 | Lyrene |
| PP12,783 | P2 | 7/2002 | Lyrene |
| PP15,146 | P3 | 9/2004 | Hancock |
| PP19,503 | P3 | 11/2008 | Lyrene |
| PP20,436 | P2 | 10/2009 | Caster et al. |
| PP20,449 | P2 | 11/2009 | Caster et al. |
| PP20,488 | P2 | 11/2009 | Caster et al. |
| PP24,407 | P3 | 4/2014 | Caster et al. |
| PP24,489 | P3 | 5/2014 | Lyrene et al. |
| PP24,568 | P3 | 6/2014 | Caster et al. |
| PP24,569 | P3 | 6/2014 | Caster et al. |
| PP24,605 | P3 | 7/2014 | Caster et al. |
| PP26,287 | P3 | 1/2016 | Caster et al. |
| PP26,451 | P3 | 3/2016 | Rodriguez et al. |
| PP26,537 | P3 | 3/2016 | Caster et al. |
| PP26,643 | P3 | 4/2016 | Caster et al. |
| PP26,748 | P3 | 5/2016 | Rodriguez et al. |
| PP27,622 | P3 | 1/2017 | Caster et al. |
| PP28,933 | P2 | 2/2018 | Caster et al. |
| PP31,649 | P2 | 4/2020 | Caster et al. |
| PP31,650 | P2 | 4/2020 | Caster et al. |
| PP31,685 | P2 | 4/2020 | Mowrey et al. |
| PP31,698 | P2 | 4/2020 | Mowrey et al. |
| PP32,267 | P2 | 10/2020 | Caster et al. |
| PP32,744 | P3 | 1/2021 | Caster et al. |
| PP32,876 | P2 | 3/2021 | Mowrey et al. |

*Primary Examiner* — Kent L Bell
(74) *Attorney, Agent, or Firm* — Morrison & Foerster LLP

(57) ABSTRACT

A new and distinct variety of blueberry plant named 'DrisBlueTwentySix', particularly selected for the sweet flavor, firmness, and large size of its fruit, its adaptability for production in low latitudes, and appearance with persistent bloom, is disclosed.

5 Drawing Sheets

Latin name: Botanical classification: *Vaccinium corymbosum* L.

Varietal denomination: The varietal denomination of the claimed variety of blueberry plant is 'DrisBlueTwentySix'.

BACKGROUND OF THE INVENTION

Blueberry plants are perennial flowering plants with indigo-colored berries from the section *Cyanococcus* within the genus *Vaccinium*. Many commercially sold species with English common names, including blueberry, are currently classified in section *Cyanococcus* of the genus *Vaccinium* and come predominantly from North America. Many North American native species of blueberries are grown commercially in the Southern Hemisphere in Australia, New Zealand, and South American nations.

*Vaccinium corymbosum*, the northern highbush blueberry, is a North American species of blueberry which has become a food crop of significant economic importance. It is native to eastern Canada and the eastern and southern United States, from Ontario east to Nova Scotia and south as far as Florida and eastern Texas. It has been naturalized in Europe, Japan, New Zealand, and the Pacific Northwest of North America. Other common names include blue huckleberry, tall huckleberry, swamp huckleberry, high blueberry, and swamp blueberry.

Blueberries are usually erect, prostrate shrubs that can vary in size from approximately four inches to approximately 13 feet in height. In the commercial production of blueberries, the smaller species are known as "lowbush blueberries", while the larger species are known as "highbush blueberries".

Blueberry bushes typically bear fruit in the middle of the growing season. However, fruiting times can be affected by local conditions such as altitude and latitude. As such, peak crop can vary from May to August in the northern hemisphere, depending upon these conditions.

Blueberries are a popular fruit that is typically consumed as fresh fruit, individually quick frozen (IQF) fruit, or in prepared foods, such as purées, juices, jellies, jams, baked goods, snack foods, and cereals.

Blueberry is an important and valuable fruit crop. Accordingly, there is a need for new varieties of blueberry plant. In particular, there is a need for improved varieties of blueberry plant that are stable, high yielding, and agronomically sound.

SUMMARY OF THE INVENTION

In order to meet these needs, the present invention is directed to an improved variety of blueberry plant. In particular, the invention relates to a new and distinct variety of blueberry plant (*Vaccinium corymbosum* L.), which has been denominated as 'DrisBlueTwentySix'.

Blueberry plant variety 'DrisBlueTwentySix' was discovered in Hillsborough County, Fla. in April of 2013 and originated from a cross between the proprietary female parent blueberry plant '196H3' (unpatented) and the proprietary male parent blueberry plant '7J301' (unpatented). The original seedling of the new variety was first asexually propagated via. softwood cuttings and shoot tissue culture in Santa Cruz County, Calif. in July of 2013.

'DrisBlueTwentySix' was subsequently asexually propagated via softwood cuttings and shoot tissue culture and underwent further testing in Santa Cruz County. Calif. for 4 years (2016 to 2020). The present blueberry variety has been found to be stable and reproduce true to type through successive asexual propagations via softwood cuttings and shoot tissue culture.

'DrisBlueTwentySix' was selected for the sweet flavor, firmness, and large size of its fruit, its adaptability for production in low latitudes, and appearance with persistent bloom. 'DrisBlueTwentySix' is a strongly evergreen variety with early and high yield when grown under low latitude conditions. Fruit are extremely large, firm, and have crisp texture with sweet flavor. Appearance is great after shipping due to persistent and heavy bloom. Plants are precocious and fruit on both one year and current season growth.

BRIEF DESCRIPTION OF THE DRAWINGS

This new blueberry plant variety is illustrated by the accompanying photographs. The colors shown are as true as can be reasonably obtained by conventional photographic procedures. The photographs are of plants that are six years old, unless otherwise specified.

DETAILED BOTANICAL DESCRIPTION

Figure 1:
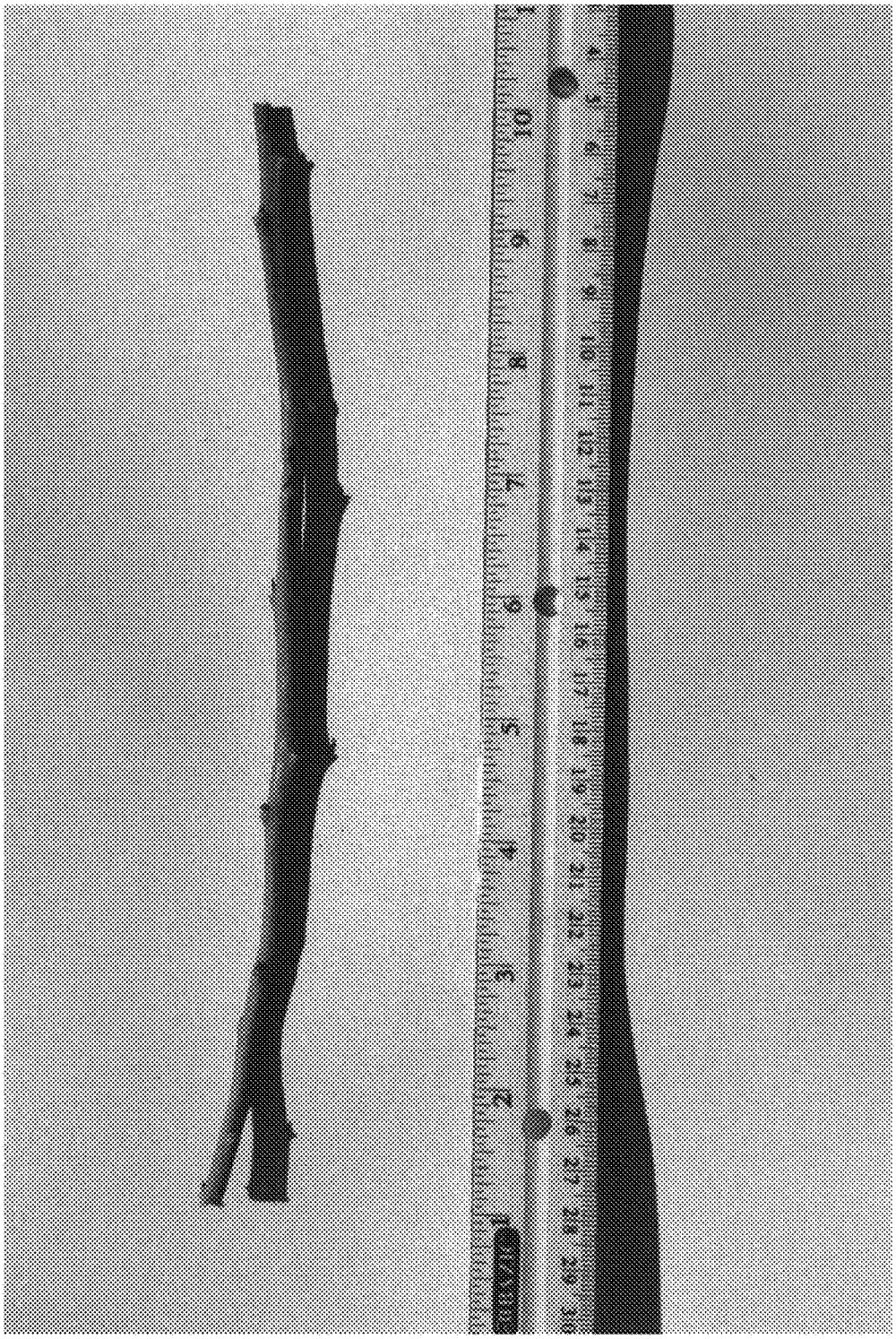
FIG. 1 illustrates a section of a cane of variety 'DrisBlueTwentySix'.
Figure 2:
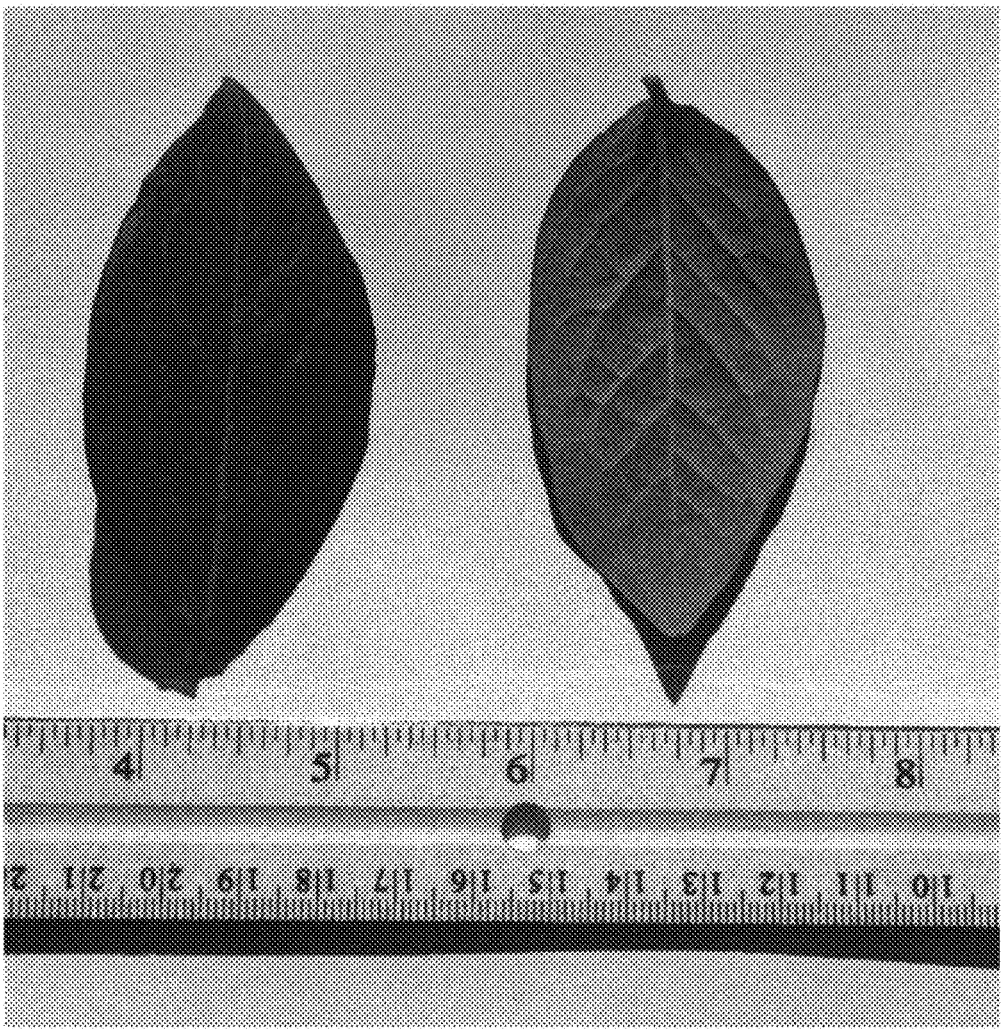
FIG. 2 illustrates leaves of variety 'DrisBlueTwentySix'. The leaf on the left shows the upper leaf surface and the leaf on the right shows the lower leaf surface.
Figure 3:
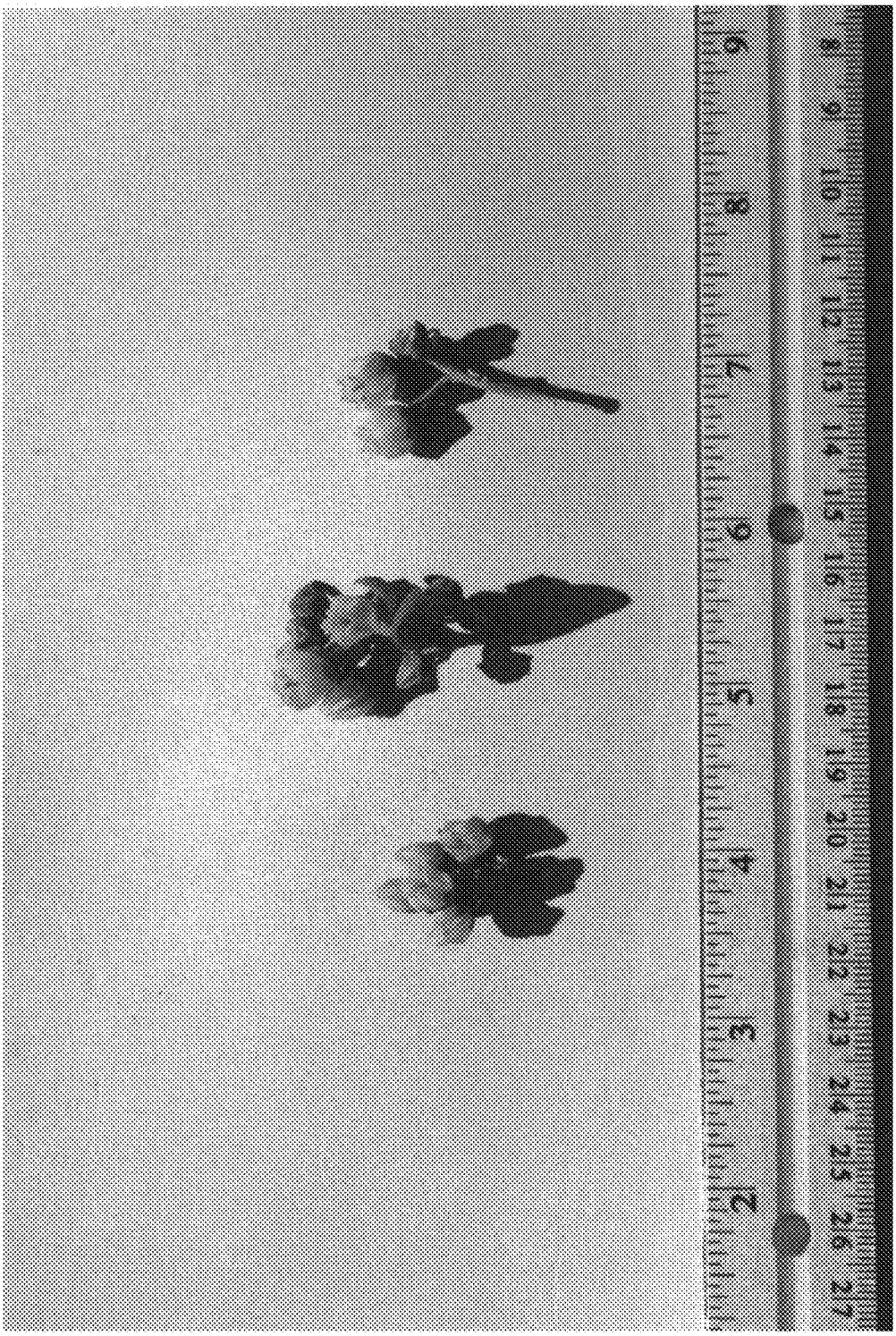
FIG. 3 illustrates clusters of flowers of variety 'DrisBlueTwentySix'.
Figure 4:
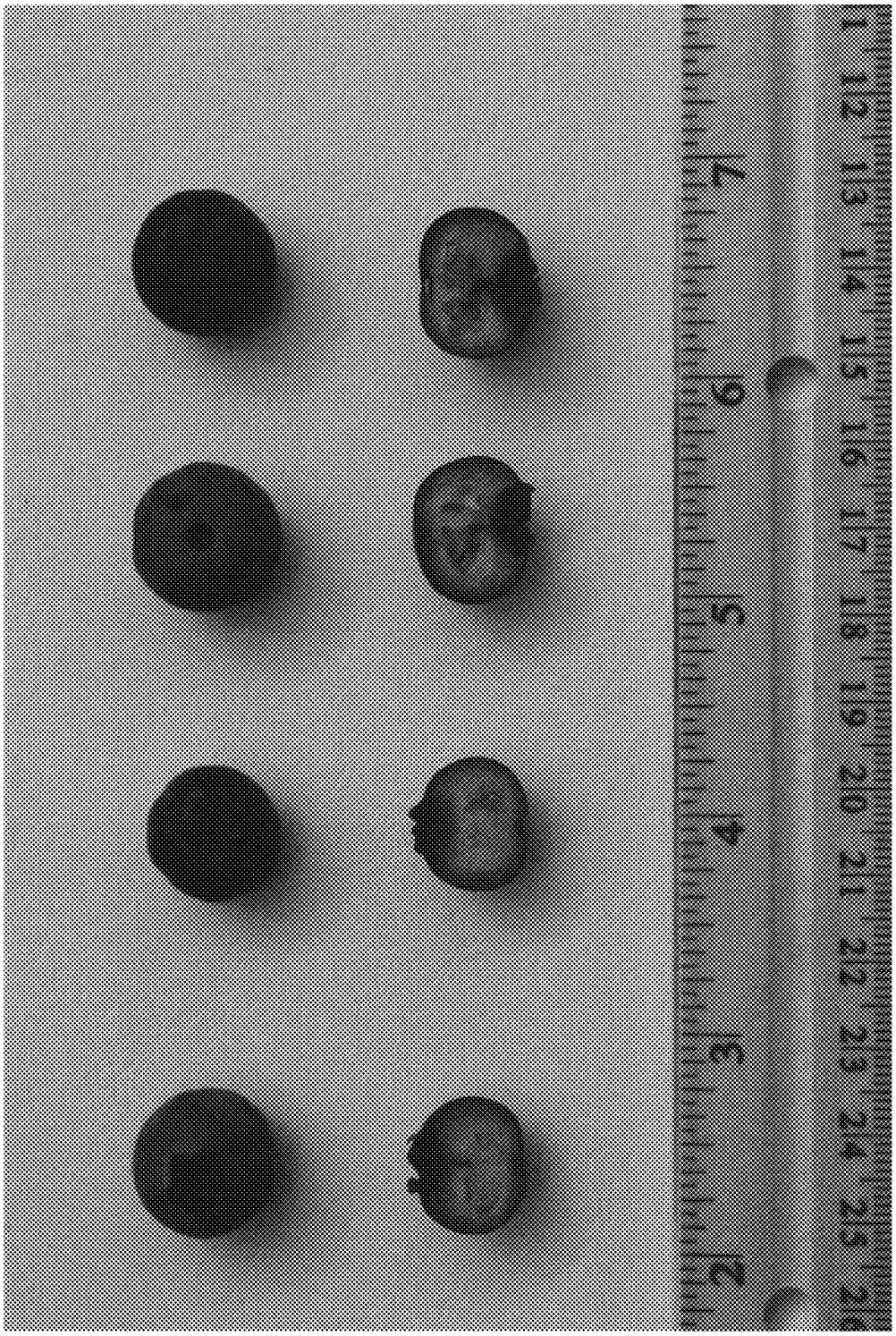
FIG. 4 illustrates whole fruits (top row) and longitudinal sections (bottom row) of variety 'DrisBlueTwentySix'. The two fruits on the top left show the top view (calyx basin) of the whole fruit, whereas the two fruits on the top right show the bottom view (fruit-pedicel junction) of the whole fruit. The first and third fruit of the top row have bloom on them, whereas the second and fourth fruit of the top row have bloom removed.
Figure 5:
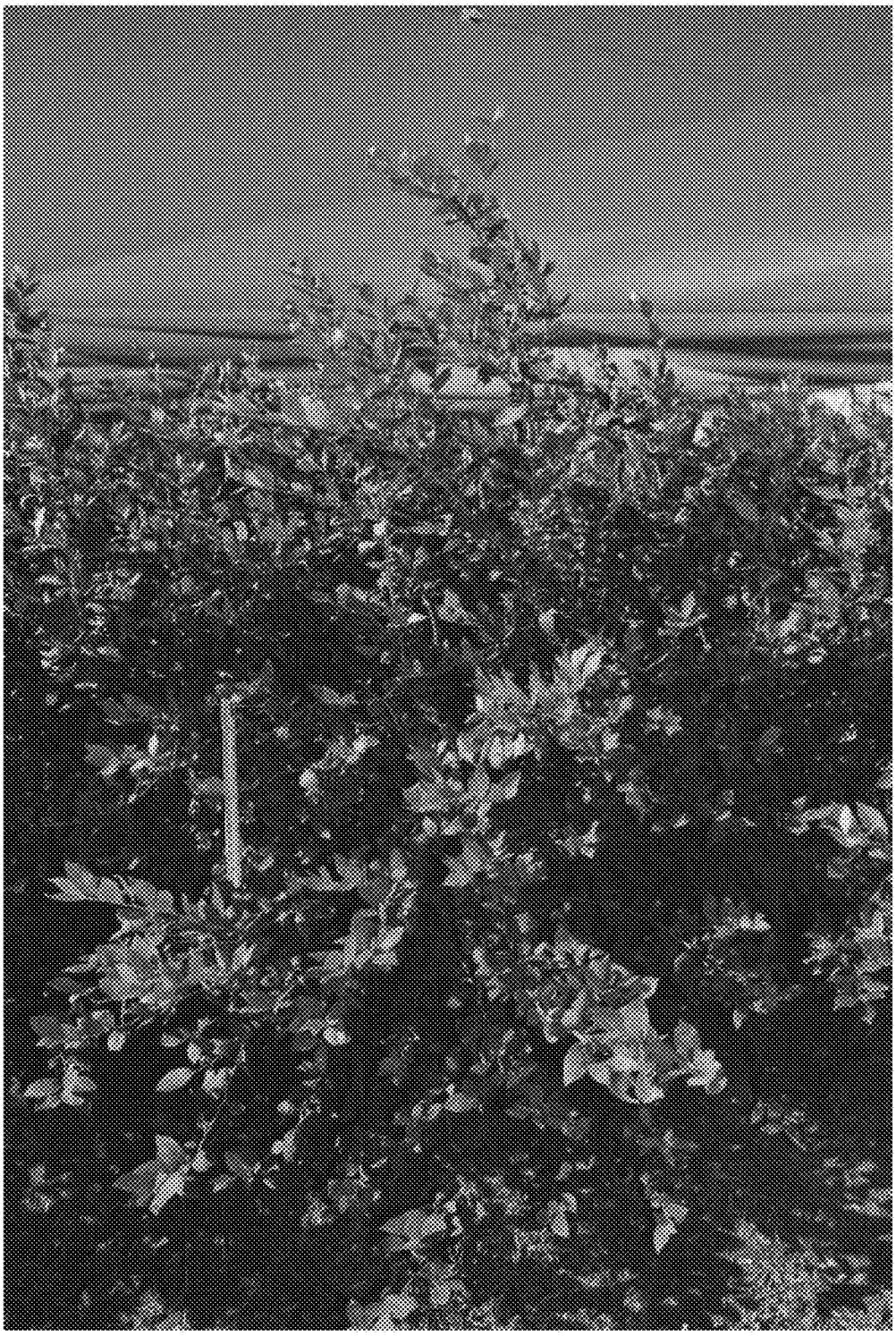
FIG. 5 illustrates whole plants of variety 'DrisBlueTwentySix'.

The following description sets forth the distinctive characteristics of 'DrisBlueTwentySix'. The data which define these characteristics is based on observations taken in Santa Cruz County, Calif. from 2016 to 2020. This description is in accordance with UPOV terminology. Color designations, color descriptions, and other phenotypical descriptions may deviate from the stated values and descriptions depending upon variation in environmental, seasonal, climatic and cultural conditions. 'DrisBlueTwentySix' has not been observed under all possible environmental conditions. Unless noted otherwise, the botanical description of 'DrisBlueTwentySix' was taken from plants that were six years old. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* 2$^{nd}$ edition by James G. Harris and Melinda Woolf Harris, unless where otherwise defined.

Classification:

*Family.*—Ericaceae.

*Botanical.*—*Vaccinium corymbosum* L.

*Common name.*—Blueberry.

*Variety name.*—'DrisBlueTwentySix'.

Parentage:

*Female parent.*—Proprietary blueberry plant '196H3' (unpatented).

*Male parent.*—Proprietary blueberry plant '7J301' (unpatented).

Plant:

*Height.*—184.9 cm.

*Width.*—147.8 cm.

*Length/width ratio.*—1.25.

*Vigor.*—Strong.

*Growth habit.*—Semi-upright.

*Cane renewal.*—Weak.

*Chilling requirements.*—'DrisBlueTwentySix' can be grown as a no-chill evergreen, but will require at least 300 hours of chilling below 7° C. for proper development if the plant goes dormant.

*Time of vegetative bud burst.*—March to April after dormancy.

*One-year-old canes* (*young canes*).—Length: 136.9 cm. Diameter at the base: 9.3 mm. Diameter at the tip: 2.2 mm. Internode length on the upper half: 21.9 mm. Color: RHS 143C (Strong yellow green). Texture: Smooth.

*Five-year-old canes* (*mature canes*).—Length: 117.1 cm. Diameter at the base: 27.8 mm. Diameter at the tip: 4.5 mm. Internode length on the upper half: 32.7 mm. Color: RHS 197C (Light greyish olive). Texture: Rough.

Leaves:

*Length.*—6.0 cm.

*Width.*—3.3 cm.

*Length/width ratio.*—1.8.

*Shape.*—Ovate.

*Margin.*—Entire.

*Apex shape.*—Cuspidate.

*Base shape.*—Cuneate.

*Arrangement.*—Alternate.

*Venation.*—Reticulate.

*Vein color.*—RHS 139B (Moderate yellowish green).

*Color on upper side.*—RHS 137A. (Moderate olive green).

*Color on lower side.*—RHS N138C (Pale greenish yellow).

*Glaucosity on upper side.*—Absent or weak.

*Trichomes on upper side.*—Glabrous (absent).

*Glossiness.*—Dull.

*Petiole.*—Length: 4.6 mm. Diameter: 2.2 mm. Color: RHS 143D (Moderate yellow green). Texture: Smooth.

*Sheath.*—Presence of leaf sheath: Present. Color: RHS 143D (Moderate yellow green). Texture: Smooth.

Flowers:

*Flower length* (*excluding pedicel*).—9.6 mm.

*Flower diameter.*—6.4 mm.

*Flower length/width ratio.*—1.5.

*Color.*—RHS 155B (Yellowish white).

*Fragrance.*—Faint.

*Inflorescence peduncle.*—Length: 22.4 mm. Diameter: 1.3 mm. Color: RHS 141D (Strong yellow green).

*Flower bud.*—Length: 6.6 mm. Width: 2.8 mm. Number of flowers per bud: 5.8. Anthocyanin coloration: Medium. Anthocyanin color: RHS 59B (Deep purplish red).

*Flower pedicel.*—Length: 7.4 mm. Diameter: 0.9 mm. Color: RHS 141D (Strong yellow green).

*Corolla.*—Shape: Ovoid. Color of corolla tube: RHS 155B (Yellowish white). Anthocyanin coloration of corolla tube on outer side: Absent or very weak. Conspicuousness of ridges on corolla tube: Medium. Color of receptacle: RHS 137A (Moderate olive green). Diameter of corolla aperture: 3.3 mm. Petal: Petal width (ridge to ridge): 3.9 mm. Color: RHS 155B (Yellowish white). Sepal: Length: 2.8 mm. Width: 3.7 mm. Color: RHS 138B (Moderate yellow green).

*Reproductive organs.*—Style: Length (including stigma): 8.1 mm. Color: RHS 144B (Strong yellow green). Ovary: Color: RHS 138B (Moderate yellow green). Stamen: Length: 5.4 mm. Color: RHS 144D (Light yellow green). Pollen: Amount: Low. Pollen color: RHS 40D (Strong yellowish pink).

*Flowering interval on one-year-old shoot.*—March to April.

*Flowering interval on current season's shoot.*—November to January.

Fruit:

*Length.*—13.14 mm.

*Width.*—19.35 mm.

*Length/ width ratio.*—0.68.

*Weight.*—3.2 grams/fruit.

*Shape in longitudinal section.*—Oblate.

*Attitude of sepals.*—Straight.

*Calyx basin.*—Diameter: 7.3 mm. Depth: 3.7 mm. Diameter/depth ratio: 2.0.

*Infructescence* (*fruit cluster*).—Number of berries per cluster: 5.4. Density: Medium. Peduncle length: 45.5 mm. Peduncle diameter: 2.1 mm. Peduncle surface texture: Rough. Peduncle color: RHS 144D (Light yellow green).

*Fruit pedicel.*—Length: 8.2 mm. Diameter: 1.2 mm. Surface texture: Smooth. Color: RHS N144D (Strong yellow green).

*Color of unripe fruit.*—RHS 149D (Pale yellow green).

*Intensity of bloom.*—Strong.

*Color of skin with bloom on mature fruit.*—RHS 100D (Very light purplish blue).

*Color of skin after removal of bloom on mature fruit.*—RHS 202A (Dark greyish purple).

*Flesh color.*—RHS 145C (Light yellow green).

*Fruit firmness.*—Very firm.

*Fruit sweetness.*—High.

*Fruit acidity.*—Low.

*Seed.*—Diameter: 0.7 mm. Color: RHS 166B (Moderate reddish brown). Abundance: Medium.

*Fruiting.*—Fruiting type: On one-year-old shoots and current season's shoots. Harvest interval on one-year-old shoot: March to April. Harvest interval on current season's shoot: October to December. Yield: 1 kg to 2 kg of fruit per plant per season from 40-month old plants when grown at Santa Cruz County, Calif. Market use of fruit: Fresh market. Shipping and storage characteristics: Following harvest, fruit can be stored for 21 days when maintained under cooled temperatures that are standard for blueberry storage.

Resistance to abiotic stress, pests, and diseases:

*Heat.*—Moderately susceptible.

*Cold resistance/USDA Hardiness Zone.*—Plants can be grown in USDA Hardiness Zone 9b (25 to 30° F./−3.9 to −1.1° C.).

*Spotted-wing drosophila* (*Drosophila suzukii*).—Moderately susceptible.

*Botrytis fruit rot* (*Botrytis cinerea*).—Moderately resistant.

*Powdery mildew* (*Podasphaera macularis*).—Moderately susceptible.

COMPARISONS TO PARENTAL, SIBLING, AND REFERENCE BLUEBERRY VARIETIES

'DrisBlueTwenty Six' differs from the female parent proprietary blueberry plant '196H3' (unpatented) in that 'DrisBlueTwentySix' has earlier production and improved plant appearance compared to '196H3'. In addition, fruit of 'DrisBlueTwentySix' is more firm and has a sweeter flavor than fruit of '196H3'.

'DrisBlueTwenty Six' differs from the male parent proprietary blueberry plant '7J301' (unpatented) in that 'DrisBlueTwentySix' has earlier production compared to '7J301', In addition, fruit of 'DrisBlueTwentySix' is more firm and larger than fruit of '7J301'.

'DrisBlueTwentySix' differs from its sibling blueberry plant variety 'DrisBlueTwentyTwo' (U.S. Plant Pat. No. 33,066) in that 'DrisBlueTwentySix' has an ovate leaf shape, a cuspidate shape of leaf apex, an ovoid shape of corolla, and a strong intensity of bloom on fruit, whereas 'DrisBlueTwentyTwo' has an elliptic leaf shape, an acute shape of leaf apex, an urceolate shape of corolla, and a medium intensity of bloom on fruit.

'DrisBlueTwentySix' differs from the reference blueberry plant variety 'DrisBlueSeven' (U.S. Plant Pat. No. 24,605) in that 'DrisBlueTwentySix' has strong plant vigor, rough texture on five-year-old canes (mature canes), an ovate leaf shape, and an ovoid shape of corolla, whereas 'DrisBlueSeven' has medium plant vigor, smooth texture on five-year-old canes (mature canes), an elliptic leaf shape, and an urceolate shape of corolla. In addition, 'DrisBlueTwentySix' has fruiting on one-year-old and current season's shoots, while 'DrisBlueSeven' has fruiting on one-year-old shoots only.

'DrisBlueTwentySix' differs from the reference blueberry plant variety 'DrisBlueThirteen' (U.S. Plant Pat. No. 26,451) in that 'DrisBlueTwentySix' has weak cane renewal, a cuspidate shape of leaf apex, dull leaves, and a strong intensity of bloom on mature fruit, whereas 'DrisBlueThirteen' has strong cane renewal, an acute shape of leaf apex, glossy leaves, and a weak intensity of bloom on mature fruit. In addition, 'DrisBlueTwentySix' has fruiting on one-year-old and current season's shoots, while 'DrisBlueThirteen' has fruiting on one-year-old shoots only.

What is claimed is:

1. A new and distinct variety of blueberry plant designated 'DrisBlueTwentySix' as shown and described herein.

* * * * *